United States Patent
Horiguchi et al.

(10) Patent No.: US 8,290,580 B2
(45) Date of Patent: Oct. 16, 2012

(54) ELECTRIC POTENTIAL THERAPEUTIC APPLIANCE, WAVEFORM SHAPING DEVICE FOR ELECTRIC POTENTIAL THERAPEUTIC APPLIANCE AND THERAPY METHOD FOR CHRONIC VIRUS INFECTIOUS DISEASE

(75) Inventors: Noboru Horiguchi, Sakaide (JP); Hiroshi Horiguchi, Sakaide (JP)

(73) Assignee: SERUMI Medical Instruments Co., Ltd.

( * ) Notice: Subject to any disclaimer, the term of this patent is extended or adjusted under 35 U.S.C. 154(b) by 0 days.

(21) Appl. No.: 10/898,328

(22) Filed: Jul. 26, 2004

(65) Prior Publication Data

US 2005/0234524 A1    Oct. 20, 2005

(30) Foreign Application Priority Data

Apr. 14, 2004    (JP) .................................. 2004-119081

(51) Int. Cl.
*A61N 1/04*    (2006.01)
(52) U.S. Cl. .................... 607/2; 607/3; 607/50; 600/9
(58) Field of Classification Search .................. 607/111, 607/115, 145, 2–3, 50; 128/898; 600/9
See application file for complete search history.

(56) References Cited

U.S. PATENT DOCUMENTS

| | | | | |
|---|---|---|---|---|
| 2,659,372 A * | 11/1953 | Andresen | ................... | 607/151 |
| 3,055,372 A * | 9/1962 | Browner | ..................... | 607/71 |
| 4,023,573 A * | 5/1977 | Pantridge et al. | .............. | 607/5 |
| 4,554,923 A * | 11/1985 | Batters | .......................... | 607/46 |
| 4,707,911 A * | 11/1987 | Kober et al. | ................. | 29/623.5 |
| 5,123,413 A * | 6/1992 | Hasegawa et al. | ............. | 607/2 |
| 5,317,155 A | 5/1994 | King | ............................. | 250/324 |
| 5,540,735 A * | 7/1996 | Wingrove | ..................... | 607/46 |
| 5,908,444 A * | 6/1999 | Azure | .............................. | 607/88 |
| 6,081,744 A | 6/2000 | Loos | ................................ | 607/2 |
| 6,214,195 B1 * | 4/2001 | Yadav et al. | ................ | 205/334 |
| 6,217,604 B1 * | 4/2001 | Azure et al. | ................. | 607/88 |
| 6,249,706 B1 | 6/2001 | Sobota et al. | ............... | 607/115 |
| 6,400,983 B1 * | 6/2002 | Cha | ................................ | 600/547 |
| 6,902,563 B2 * | 6/2005 | Wilkens et al. | ............... | 606/9 |
| 2004/0082183 A1 | 4/2004 | Mori | ........................... | 438/704 |

FOREIGN PATENT DOCUMENTS

| | | | |
|---|---|---|---|
| GB | 2372705 A | * | 9/2002 |
| JP | 11-276602 | | 10/1999 |
| JP | 2000-37437 | * | 8/2000 |
| JP | 2001-309987 | | 11/2001 |
| JP | 2001309987 | | 11/2001 |

* cited by examiner

Primary Examiner — Niketa Patel
Assistant Examiner — Joseph Stoklosa
(74) Attorney, Agent, or Firm — Rene A. Vazquez, Esq.

(57) ABSTRACT

The provision of an potential therapeutic appliance for the delivery into living organisms of highly effective negative ions similar to those found in nature; and in particular, providing a special waveform shaping device that shapes the voltage waveforms delivered to electrodes to efficiently produce negative ions, that is capable of stable performance, and that can be easily manufactured. A waveform shaping device 3 charged with an inorganic insulating powder such as pumice stone powder and a predetermined volume of moisture is disposed in series between a high voltage power supply 2 and an output terminal 12; the current output from the negative terminal of the high voltage power supply is shaped by the waveform shaping device and then delivered to the output terminal; and in a repetitive process, the charge delivered from the high voltage power supply 2 is accumulated temporarily in a terminal 4 and discharged in a burst-like manner; thus facilitating convenient action of negative ions on the human body.

5 Claims, 7 Drawing Sheets

| No. | grain size ($\mu$m) | voltage of Ion transformer (-kV) | | current ($\mu$A) | | | | ORP (mV) | ESR R2 |
|---|---|---|---|---|---|---|---|---|---|
| | | before | just after | discharge | start | 10min | 25min | | |
| 1 | tap water | — | — | | — | | | +846 | 12.80 |
| 2 | ~75 | 5.89 | 5.89 | 220 | 219 | 220 | 221 | −445 | 0.68 |
| 3 | ~106 | 5.93 | 5.89 | 220 | 70 | 256 | 256 | −452 | 0.97 |
| 4 | 106~150 | 5.87 | 5.51 | 180 | 249 | 92 | 76 | −392 | 1.33 |
| 5 | 150~250 | 5.76 | 5.36 | 110 | 175 | 189 | 56 | +214 | 4.67 |
| 6 | 250~ | 5.43 | 5.20 | 88 | 116 | 77 | 47 | +231 | 5.20 |

ELECTRIC POTENTIAL THERAPEUTIC APPLIANCE, WAVEFORM SHAPING DEVICE FOR ELECTRIC POTENTIAL THERAPEUTIC APPLIANCE AND THERAPY METHOD FOR CHRONIC VIRUS INFECTIOUS DISEASE

BACKGROUND OF THE INVENTION

1. Field of the Invention

The present invention relates to electric potential therapeutic appliances, and in particular to electric potential therapeutic appliances provided with a waveform shaping device for producing negative ions or reducing ions.

2. Description of the Related Arts

In recent years, actual proof of the effect of negative ions or reducing ions on the human body has accumulated, and rather than applying to health alone, the effect of these ions in terms of medical therapy has also been clearly accumulated. In particular, enhancement of the immunity and natural healing power inherent to humans by using the effect of the action of negative ions is expected to realize effective therapies; accordingly, electric potential therapeutic appliances providing capability to produce negative ions are currently in development.

Japanese unexamined patent laid-open JP 2001-309987A also discloses an electric potential therapeutic appliance having a function for discharging negative ions. In the electric potential therapeutic appliance of JP 2001-309987A, a therapeutic electrode provided for the purpose of electric potential therapeutics comprises a pad containing a multiplicity of holes, a needle electrode and an opposing curved plate electrode inserted in the therapeutic electrode, and corona discharge is made to occur; accordingly, simultaneous with the setting of the electrode pad to a high electric potential compared to the earth and the administering of electric potential therapeutics, the negative ions produced inside the therapeutic electrode are supplied from the holes provided in the pad to the patient through the skin.

Although the production of large amounts of negative ions is sought after in this type of electric potential therapeutic appliance, the benefit thereof in terms of therapy cannot necessarily be guaranteed when, for example, coronal discharge is used to produce large amounts at any cost. The effective intake of electrons or electrical charges produced by an electric potential therapeutic appliance into living organisms in order that these organisms may actually benefit from the effect of negative ions is important in nature.

The qualities of produced negative ions are important with regard to the imparting of these ions to living organisms, and it is preferable that these ions have similar mobility to negative cluster ions occurring as a natural phenomenon in the atmosphere. Here, mobility refers to the speed of ions in an electric field and represents the ease of motion of negative ions; accordingly, when mobility is high, chemical reactions with other substances will occur more readily, and even reduction or alkalization occurs more easily in the atmosphere. Negative ions comprising of cluster ions generally have high mobility, and they are thought to have the corresponding suppressive effect on acidification and oxidation.

Rather than uniformly discharging electrons or electrical charges in order to artificially produce negative ions with high mobility, it is more effective to allow the charge to build up to a certain degree and to then carry out burst-type discharge. Furthermore, negative ions produced in the atmosphere through the use of this intermittent discharge method remain for long periods after the end of discharge and have been observed as having long life spans. It is also known that by using a mechanism expected to efficiently produce negative ions in the atmosphere and directly imparting the produced charges to living organisms, the negative ion effect can be realized in body fluids and benefits in terms of therapy or constitution can be achieved.

These facts are also described in the specification of Japanese patent application 2003-283103 as disclosed by the present applicants. The invention disclosed by the present applicants in the above specification achieved the same effect using a waveform shaping device formed by filling pumice stone masses containing specific amounts of moisture. In this waveform shaping device, it is necessary that the size of the filled pumice stone masses shows the predetermined distribution by adjusting the size of the pumice stone masses, and the electrical characteristics is adjusted to specific values by controlling pressure while monitoring the voltage drop generated between terminals when a container is sealed; accordingly, an experienced operator must spend a considerable amount of time in the production process.

SUMMARY OF THE INVENTION

An object of the Invention is to provide electric potential therapeutic appliances for supplying highly effective negative ions in living organisms similar to those found in nature; it is another object of the invention to provide both a special waveform shaping device that shapes the voltage waveforms supplied to electrodes into efficiently produce negative ions, that is capable of stable performance, and that can be easily manufactured; and it is another object of the invention to provide an electric potential therapeutic appliance provided with such a special waveform shaping device.

In order to attain the objects explained above, the electric potential therapeutic appliance according to the present invention comprises a waveform shaping device filled with inorganic insulating powder and a predetermined amount of moisture, and arranged in series between a high voltage power supply and an output terminal, for supplying the output current output from a negative terminal of the high voltage power supply to the output terminal via this waveform shaping device.

In order that negative ions may more easily produce an effect in the human body, favorable results can be achieved by repeating a process wherein burst-type discharge is performed after accumulating charge in electrodes at a stroke rather than applying a fixed electric field to continually supply negative charges from the high voltage circuit as in the conventional arts.

While a waveform shaping device providing a condenser for storing the charge and a high-speed switch short-circuiting the end plates of the condenser can be used to accumulate charge and to perform intermittent discharge, high precision mechanisms are required to allow suitable operation while adjusting the voltage level and/or charge volume, or the like to suitable magnitudes using an adjustable waveform shaping device capable of adjustment; accordingly, such devices are expensive in nature. As a result of various studies, the inventors of the present invention obtained a waveform shaping device with a simple construction and capable of producing negative ions more efficiently.

In other words, the waveform shaping device used in the present invention seals a charge of inorganic insulating powder and a predetermined amount of moisture between a pair of electrode plates. Although this waveform shaping device is constituted of a condenser formed into a prescribed shape from a charge of inorganic powder with insulating properties, the surfaces of the powder particles contain a suitable amount of moisture that they do not become wet, causing them to become slightly conductive. When a high voltage is then applied between the electrode plates, charge accumulates in accordance with the electrical capacitance; however, as a result of the subsequent breakdown of resistance characterized by the withstand voltage being exceeded, the charge passes between the electrode plates and current flows. When the voltage between the electrode plates drops as a result of the discharge, the insulation property is recovered and the accumulation of charge begins once again, and when the potential difference between the terminals reaches a predetermined voltage, the breakdown of resistance and the resulting energization occurs again.

By applying a high voltage between the two terminals of a waveform shaping device constructed in this way, an energizing element supplying current with a substantially fixed cycle can be realized. However, even during energization as a result of dielectric breakdown, there is a high degree of resistance between the terminals, therefore, the current supplied is not large.

When reducing water is produced by supplying to water the intermittent current output obtained by forming a high voltage power output such that the waveform shaping device intervenes between them, and when this reducing water is added to hydroxyl radical active oxygen produced by Fenton reaction, the volume of remaining hydroxyl radicals is greatly reduced. When this is acted on raw water with an ORP value of +800 mV, it reaches to a level between approximately −300 mV and −400 mV. Furthermore, the amount of dissolved hydrogen within the city water also increases greatly by adding this reducing water.

Conversely, when a similar test is carried out using a direct current high negative voltage generator not having a waveform shaping device, the ORP value in particular reduces by a certain degree to approximately +500 mV; however, almost no change is identified in the volume of hydroxyl radicals, the volume of dissolved hydrogen is also unchanged, and this is less than expected in terms of reducing strength. In this way, it was confirmed that water to which electrical charges were supplied via the waveform shaping device according to the present invention has a significant effect on controlling active oxygen and considerable reducing strength.

In addition, when the intermittent current or intermittent electrical field produced using the electric potential therapeutic appliance according to the present invention is applied to a living organism via probe electrode plates, negative ions are produced therein and in vivo alkalization and reduction is promoted, providing considerable support to the therapy of diseased areas, furthering therapy, and improving health.

When negative ion exposure is carried out with respect to healthy adult subjects using electric potential therapeutic appliances providing the waveform shaping device and the activity of natural killer (NK) cells in peripheral blood is compared between before and after exposure, even when, for example, the activity was 38% before exposure, it increased to 53% thereafter with a significant difference.

Furthermore, the condition of the inorganic insulating powder and quantity of the water filled in the waveform shaping device have a peak effect with respect to the production of negative ions; in particular, the performance of negative ion production is good when porous powder with grain sizes of between 1 μm and 200 μm is used, and in addition, this is also improved when the charge includes between 2.5% and 3.5% of moisture by volume. Above all, more favorable results can be achieved when the grain size of the inorganic insulating powder is 75 μm or less. Pulverized pumice stone can be used as porous powder.

It is accepted that the higher the negative potential applied using the electric potential therapeutic appliance the better, and whereas potential in the range of −9 kV was applied using technology known in the prior art, while the waveform shaping device according to the present invention allows the range in which cluster ions produced by electrons discharged from the electrode can demonstrate favorable reduction to be reduced to approximately −3 kV, thus realizing a device that is extremely easy to use.

When applying the electric potential therapeutic appliance according to the present invention with respect to living organisms, there is a need for low invasiveness and for an ample amount of negative ions to be produced in vivo. Accordingly, when functioning as a reducing-ion water production device, adjustment is first of all carried out to ensure ORP values of between −400 and −500 mV, the probe electrode plates are then connected, and the electric field is applied to the human body. At this time, the current passing through the electrodes immersed in water in order to produce reducing water is approximately 200 μA.

The probe electrode plates making contact with the body have a construction comprising insulating rubber and conductive rubber layered on a metal electrode plate, and the current can be controlled to as little as between 0.1 and 10 μA, thus introducing as large a volume of negative ions as possible into the body and ensuring the safety of the human body.

As a result of its ability to produce an extremely large amount of negative ions in vivo, the electric potential therapeutic appliance according to the present invention was seen to induce activation of immune responsive cells. Accordingly, by applying the electric potential therapeutic appliance according to the present invention with respect to a patient infected with a chronic viral disease, the immunity thereof can be activated, the in vivo amount of virus can be reduced, and symptoms can be alleviated. In particular, immune responsive cells can also be activated in patients infected with human immunodeficiency virus (HIV), allowing the in vivo amount of HIV to be reduced.

It is preferable for the electric potential therapeutic appliance according to the present invention to apply a negative potential to a palm sandwiched between the ground side probe electrode plate and the negative potential probe electrode plate. The palm is relatively thin and contains a large flow of blood; accordingly, this configuration is characterized by a small distance between the probe electrode plates, a strong electric field, and a significant effect achieved through powerful action on a large volume of blood. Furthermore, as the hand is normally exposed, the probe electrode plates can be easily applied thereto, thereby the burden on patients and technicians can be reduced.

In comparison with the usage of electric potential therapeutic appliances known in the prior art, the electric potential therapeutic appliance according to the present invention dramatically increases the concentration of in vivo reducing ions, eliminates active oxygen, preserves alkalization of blood, prevents red blood cells from forming rouleaux formations, and promotes better circulation; consequently, natural healing power can be enhanced and effective therapy for various diseases can be realized. In particular, significant results are promised by the present invention with respect to human immunodeficiency virus, which is difficult to treat and prone to side effects as a result of chemical therapy.

DETAILED DESCRIPTION OF THE PREFERRED EMBODIMENT

Figure 1:
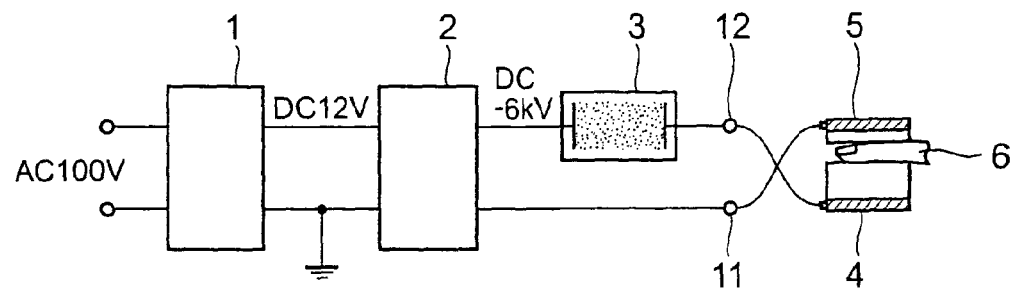
FIG. 1 is a block diagram showing one embodiment of an electric potential therapeutic appliance according to the present invention.

As a result of research by the inventors of the present invention and as described, for example, in the specification of Japanese patent application 2003-283103, a beneficial effect in terms of the production efficiency and condition of negative ions can be achieved by disposing a waveform shaping device containing a charge of porous inorganic bodies together with a small amount of water so as to intervene in series to the negative terminal of a high voltage power source, and by applying current to water or the human body.

In practical situations, particularly beneficial results can be obtained using pumice stone. In the device disclosed in the above-mentioned specification, the porous nature of pumice stone is utilized, and before the grains of pumice store are packed in a case, they are placed for an extended period of time, for example, in a bath held at constant-temperature and humidity so that a suitable amount of water is permeated to the interior of the pores and the electrical characteristics thereof are adjusted to the desired levels; subsequently, suitable volumes of grains of a relatively large size and grains of a relatively small size are taken out and mixed, and grains of pumice stone having a suitable grain size distribution are packed into the case.

When pressure is applied to the cover disposed above the grains of pumice stone packed into the case during preparing the waveform shaping device, the output voltage changes; accordingly, a predetermined voltage is applied to the input lead, the force of pressure is adjusted while monitoring the voltage present in the output lead, the voltage is set to the optimum range as determined by testing, and the cover is then secured in place using adhesive.

Upon measurement of the frequency characteristics of a waveform shaping device so obtained, the low frequency band was seen to have high resistance and capacity while the high frequency band was seen to have progressively lower resistance and capacity; furthermore, a sudden switch to low resistance and high capacity was identified at above 50 MHz.

When a negative high voltage DC output is passed through this waveform shaping device and the current obtained at the output terminals thereof is applied to water, reducing ions with a high reducing strength are produced. Furthermore, when current from the output terminals is applied to the air in a room to produce and provide air including negative ions, it has been determined that the blood indices of the subjects in the room are significantly increased and the subjects' bodies experience a beneficial effect. However, careful work by a skilled technician is required in order to produce this type of product.

Undertaking even more diligent research, the inventors of the present invention discovered a remarkably effective material and manufacturing conditions facilitating simple production without the need for high-level skills. Hereinafter, the electric potential therapeutic appliance and waveform shaping device according to the present invention will be described by way of the preferred embodiment thereof.

Figure 2:
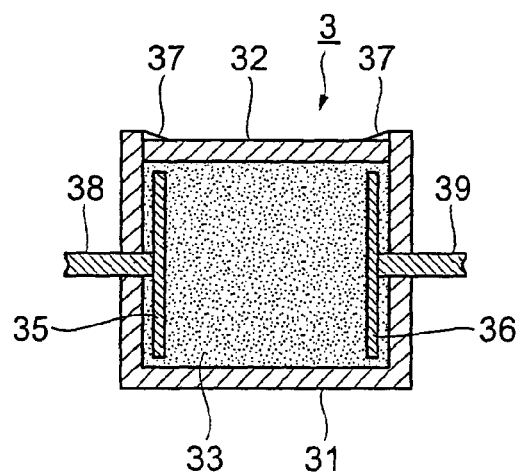
FIG. 2 is a cross sectional view of a waveform shaping device used in the present embodiment.
Figure 3:
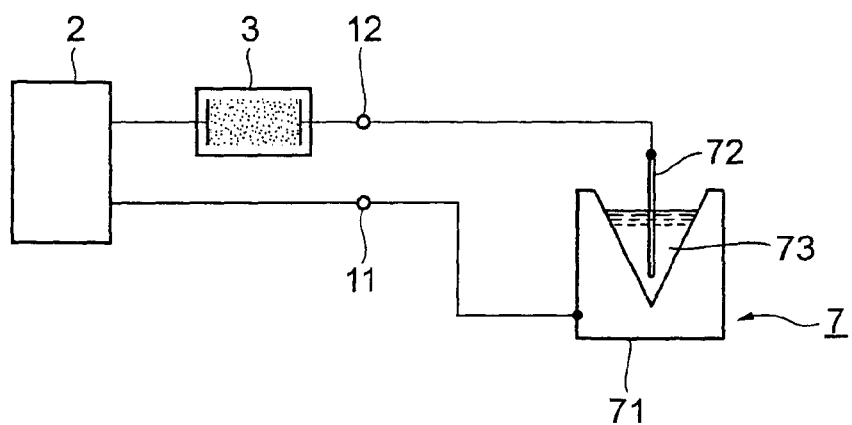
FIG. 3 is a block diagram of a system for inspecting the substitution performance of the electric potential therapeutic appliance of the present embodiment.
Figures 4, 5:
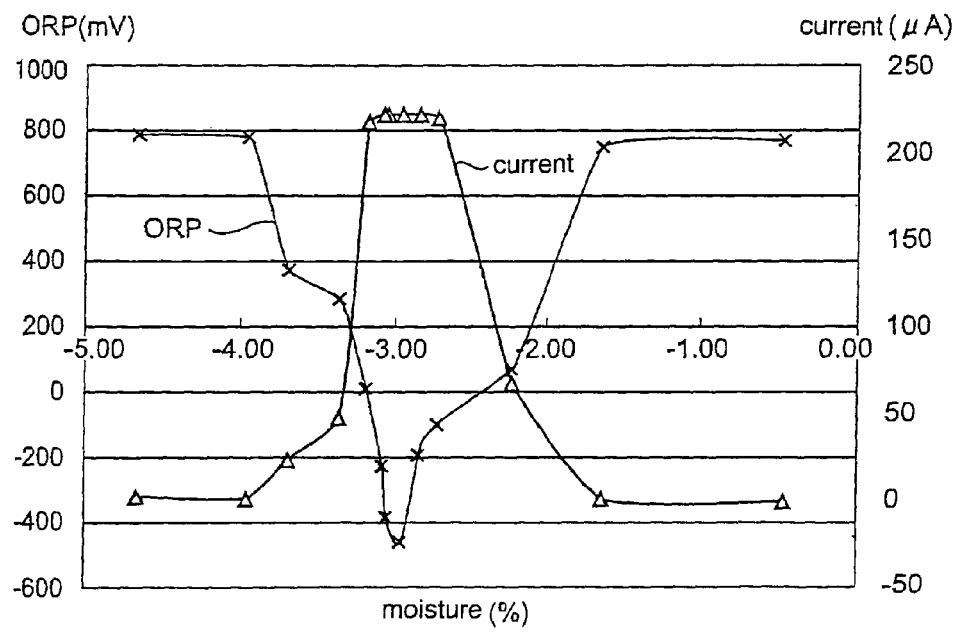
FIG. 4 is a table showing the relationship between the grain size of powder charged into the waveform shaping device of the present embodiment and the performance thereof.
FIG. 5 is a graph showing the relationship between the amount of moisture in the waveform shaping device of the present embodiment and the performance thereof.
Figure 6:
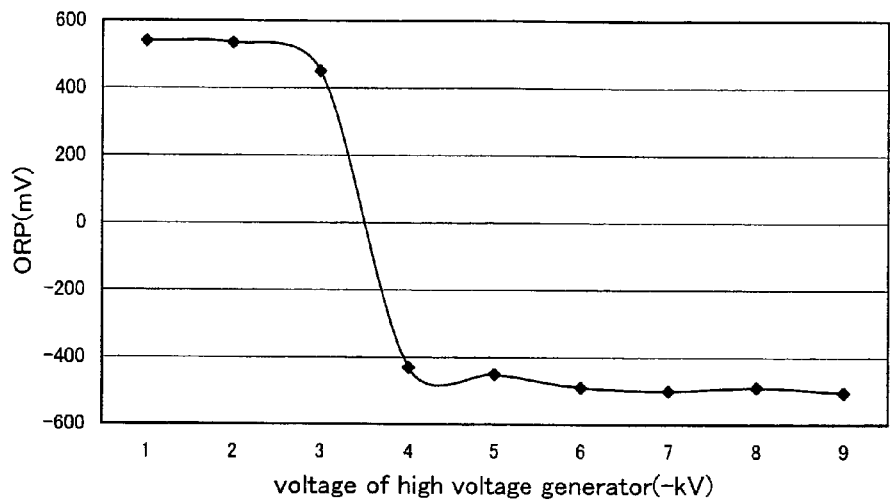
FIG. 6 is a graph showing the relationship between the application voltage and water ORP value in a situation where negative ion water is produced using the waveform shaping device of the present embodiment.
Figure 7:
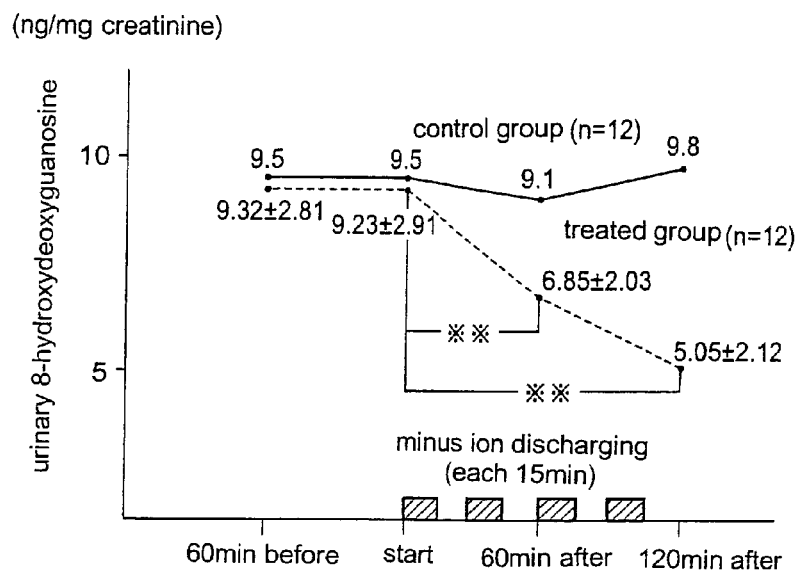
FIG. 7 is a graph showing the change over time of 8-OHdG in urine when the electric potential therapeutic appliance of the present embodiment is applied to humans.
Figure 8:
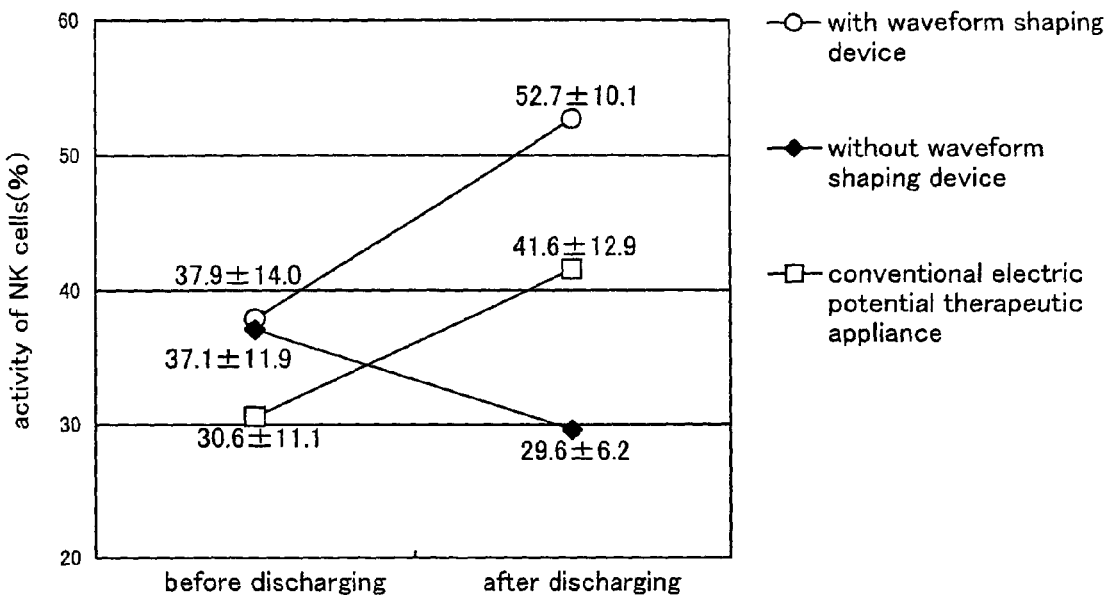
FIG. 8 is a graph showing the effect on NK cell activity when the electric potential therapeutic appliance of the present embodiment is applied to humans.
Figure 9:
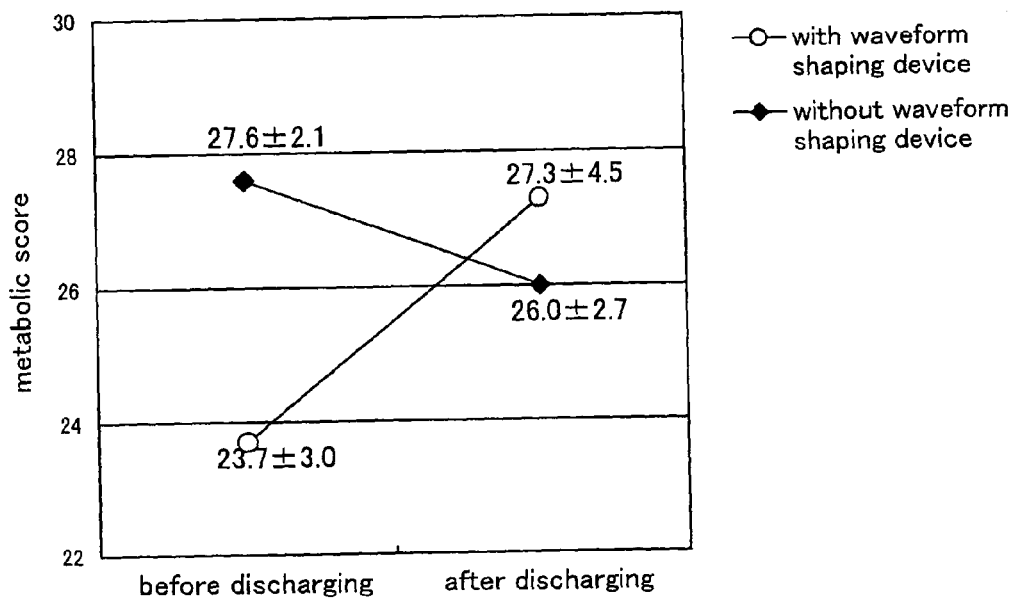
FIG. 9 is a graph showing the results of metabolic scoring when the electric potential therapeutic appliance of the present embodiment is applied to humans.
Figure 10:
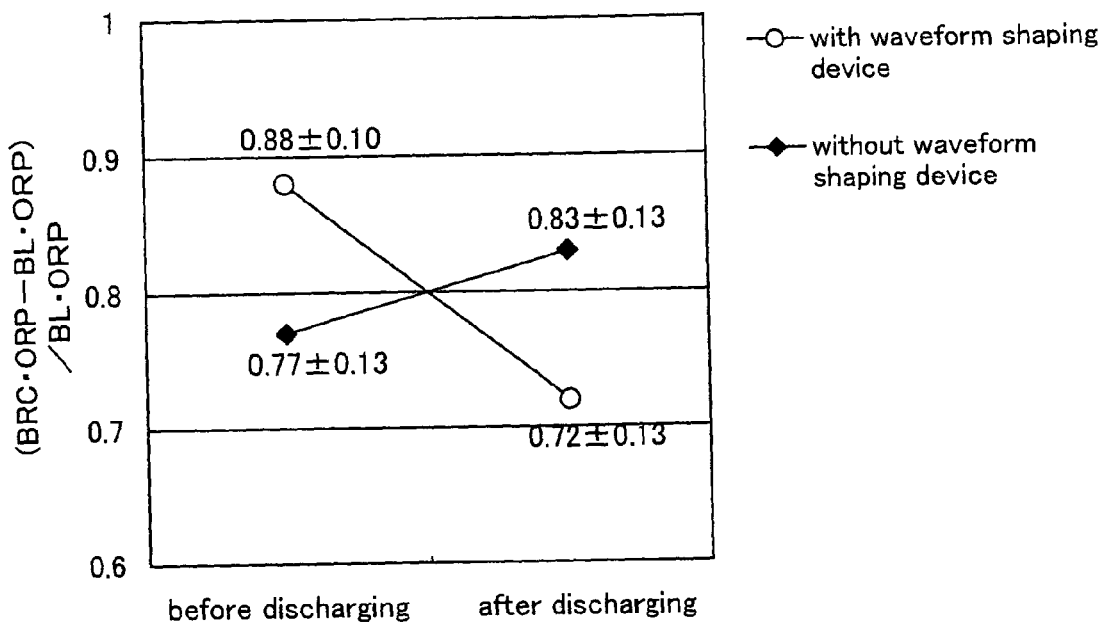
FIG. 10 is a graph showing results regarding the relationship between intra-cellular and extra-cellular ORP values when the electric potential therapeutic appliance of the present embodiment is applied to humans.
Figure 11:
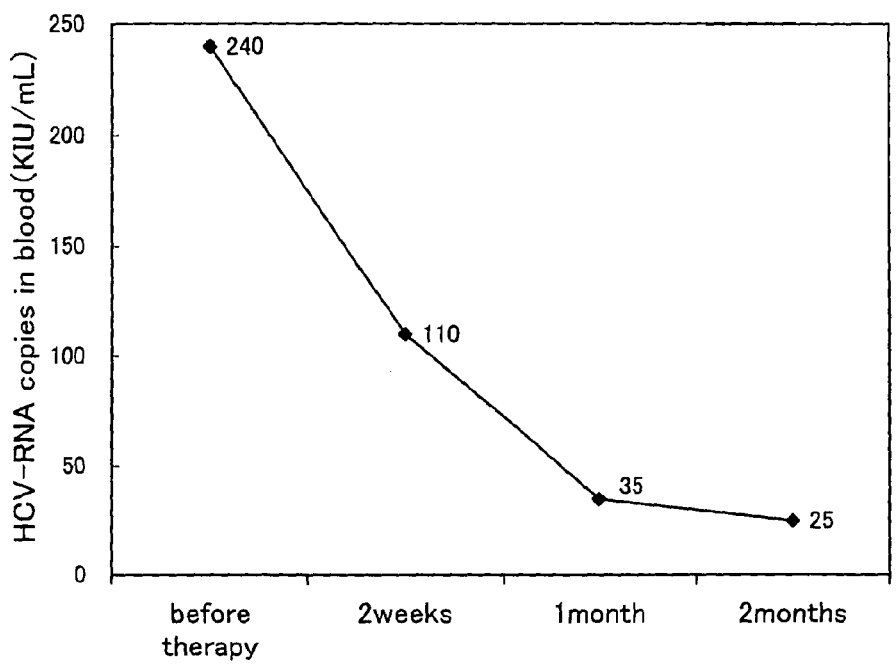
FIG. 11 is a graph showing the change over time of the number of HCV-RNA copies in the blood of a subject infected with hepatitis C virus when therapy is administered using the electric potential therapeutic appliance of the present embodiment.

FIG. 1 is a block diagram showing an electric potential therapeutic appliance according to one embodiment of the present invention; FIG. 2 is a cross sectional view of a waveform shaping device according to one embodiment of the present invention; FIG. 3 is a block diagram of a device for performance testing using a negative ion producing device in terms of the electric potential therapeutic appliance according to the present embodiment; FIG. 4 is a table showing the change in performance upon variation of the grain size of powder changed in the waveform shaping device of the present embodiment; FIG. 5 is a graph showing the change in performance upon variation of the amount of moisture inside the waveform shaping device; FIG. 6 is a graph showing results obtained by monitoring the water ORP value of a negative ion producing device when the application voltage of the waveform shaping device is varied; FIG. 7, FIG. 8, and FIG. 9 are graphs showing test results obtained by measuring the effect on the human body of application of the electric potential therapeutic appliance according to the present embodiment; FIG. 10 is a diagram showing an example of usage of the present embodiment; and FIG. 11 is a conceptual illustration an example of the construction of a probe electrode plates used in the present embodiment.

As shown in FIG. 1, the electric potential therapeutic appliance according to this embodiment of the present invention incorporates a waveform shaping device as shown in FIG. 2 into the electric potential therapeutic appliance of the conventional format, and by transforming the potential output waveform into a special shape and realizing the effect of negative ions or reducing ions in the human body, enhances the health of the subject and cures diseases.

The electric potential therapeutic appliance according to this embodiment comprises as principal elements a power adaptor 1, a direct current high negative voltage generator 2, a waveform shaping device 3, a negative probe electrode plate 4, and an earth electrode plate 5.

The power adaptor 1 constitutes an AC to DC converter converting alternating current at 100 V to supply direct current at 12 V. The 0 V output terminal thereof is grounded. The direct current high negative voltage generator 2 is a voltage booster device using an electromagnetic coil and a rectifier, and when the +12V DC power supply is supplied from the power adaptor 1, this is alternated by a high-frequency chopping circuit, boosted in the coil, subjected to full-wave rectification, planarized by the capacitor, and supplied from the output terminals as negative high voltage direct current. Adjustment of the output voltage is possible, and for example, direct current of up to −9 kV can be supplied.

The negative high voltage terminal of the direct current high negative voltage generator 2 is connected to the input terminal of the waveform shaping device 3. The waveform shaping device 3 is a capacitive distributed constant circuit element with high resistance, providing, for example, the construction shown in FIG. 2, shaping high voltage direct current signals, and supplying intermittent current. The negative probe electrode plate 4 is connected to the output terminal 12 of the waveform shaping device 3, and the earth electrode plate 5 is connected to the earth terminal 11 of the direct current high negative voltage generator 2.

The finger(s) 6, the palm or the like of the subject are fixed in contact between the negative probe electrode plate 4 and the earth electrode plate 5, and an electric field corresponding to the output voltage of the waveform shaping device 3 is applied. Consequently, the effect of negative ions is realized in the subject's body, and health is enhanced by alkalizing the blood thereof, by producing a reducing effect, by suppressing active oxygen, and the like.

The waveform shaping device 3 as shown in FIG. 2 constitutes one example of a waveform shaping device used in this embodiment, and for example, comprises a sealed space realized using an electrically non-conductive case 31 and inner cover 32 made of synthetic resin, and wherein a predetermined amount of moisture is contained and a porous inorganic insulating powder 33 are filled therein.

A pair of electrode plates 35, 36 are provided within the case 31 on the walls thereof enclosing the inorganic insulating powder 33. One of the electrode plates 35 is connected to the negative high voltage terminal of the direct current high negative voltage generator 2 via a lead 38, and the other electrode plate 36 is connected to the negative probe electrode plate 4 via a lead 39. The cover 32 is affixed to the case 31 using adhesive 37, sealing the waveform shaping device 3.

Because high voltages of several kilovolts are applied between the pair of electrode plates, the inorganic insulating powder 33 must have insulating properties. In addition, it is preferable that the material thereof be wettable and preserves moisture on the surface thereof. Rather than being a complete resistor, when a high voltage is applied to the dampened inorganic insulating substance charged between the electrode plates and making intimate contact therewith, a phenomenon similar to the breakdown of resistance occurs, a small amount of current flows; furthermore, when the voltage drops, the insulating condition is restored. The pulsating condition created using a waveform shaping device with this type of non-linear characteristic is used to efficiently produce negative ions.

Powders of silicon dioxide $SiO_2$, aluminum oxide $Al_2O_3$, and other similar pure inorganic compounds can be used as the inorganic insulating powder. In particular, it is preferable that powder produced by finely pulverizing pumice stone be used. Pumice stone comprises insulating substances such as silicon dioxide and aluminum oxide, and being both porous and brittle, it can easily be pulverized depending on its porous nature and fragility. The grains of powdered pumice stone have large inner surface in the grains in addition of the outer surface which can hold moisture; consequently, thereby the powdered pumice stone can be given a suitable electrical resistance.

Although pumice stone is charged into the waveform shaping device disclosed in the specification of Japanese patent application 2003-283103, the combination of pumice stone powders with differing grain sizes, adjustment of the amount of moisture, the control of pressure in order to adjust the output voltage, and other subtle adjustments were made in the production process; accordingly, a mastery of the corresponding techniques was required.

However, the waveform shaping device according to the present embodiment uses a powder-form inorganic insulating substance as explained above. Consequently, by simply charging a single type of prepared powder to a container, uniformity can be maintained within the waveform shaping device, and by adjusting the moisture volume, the desired qualities can be easily realized.

However, since the powder shape affects the output, it is necessary to select the optimum grain size and wetness. The inventors of the present invention studied the performance of an electric potential therapeutic appliance incorporating a waveform shaping device with differing grain sizes and wetness, determining the optimum levels thereof. In order to conveniently estimate the effectiveness of an electric potential therapeutic appliance provided with the waveform shaping device according to the present embodiment, the inventors used the productivity of reducing ion water as an alternative index.

FIG. 3 is a block diagram of a test device incorporated with a reducing-ion water production device. In the reducing-ion water production device 7, water 73 is charged into an electrically conductive container 71 and a cathode needle 72 is inserted therein as shown in the right part of FIG. 3; furthermore, when a negative charge is applied to the cathode needle 72, negative ion clusters are produced in the water. In order to estimate the performance of the waveform shaping device 3, the output terminal 12 thereof is connected to the cathode needle 72, the earth terminal 11 of the electric potential therapeutic appliance is connected to the electrically conductive container 71, the electric potential therapeutic appliance is operated, and the volume of negative ion clusters produced in the water is measured.

Although the purpose of the electric potential therapeutic appliance according to the present invention is to produce reducing ions, calculation of the amount of negative ion clusters with reducing capability produced by the reducing-ion water production device 7 when the electric potential therapeutic appliance is used can be easily carried out through measurement of the oxidation reduction potential (ORP) with an ORP gauge. Reduction performance can be determined more precisely by instilling a metered dose of ionized water into hydroxyl radical active oxygen produced by the Fenton reaction, and by measuring the hydroxyl radicals remaining after the reaction using a free radical monitor (ESR).

However, the ORP value and the remaining hydroxyl radicals (i.e., the ESR value) frequently contradict each other. Differences there between are inevitable as the ORP value relates to the volumes of oxygen and hydrogen dissolved in water and the ESR value indicates the reaction activity; furthermore, although a considerable amount of effort and time is required for measurement of the ESR value, this is more suitable as an index of reducing strength. However, since the ESR value rises only when the ORP value drops, it is reasonable to use the ORP value as an alternative index for an easy method.

The table shown in FIG. 4 illustrates the variation in performance when the grain size of the powder is changed. Waveform shaping devices in which different graded sizes of powder comprising pulverized pumice stone are each charged to a cabinet with internal dimensions of 5.6 cm×2.8 cm×4.6 cm were prepared; subsequently, the high voltage power source applied to city water through these waveform shaping devices; the ORP values and the ESR values corresponding to the remaining hydroxyl radicals through the procedure described above were measured. The surface area of the internal electrode plates was 11.4 $cm^2$.

The results of measurement showed that whereas the ORP value for city water was +846 mV, the value for powder with a grain size of 250 μm or greater was +231 mV, the value for powder with a grain size of between 150 and 250 μm or greater was +214 mV, the value for powder with a grain size of between 106 and 150 μm was −392 mV, and the value for powder with a grain size of 106 μm or less was −452 mV. For comparison, the ORP value for hydrogen is −420 mV, and the ORP value for oxygen is +815 mV.

With regard to the ESR value at this time, whereas the value for city water was 12.80, the value was gradually reduced as the grain size reduced, such as the value was 4.674 for powder with a grain size of between 150 and 250 μm, and 0.9733 for particles with a grain size of 106 μm or less. As a result of closer examination, it was seen that when powder with a grain size of 75 μm or less was used, the ORP value was sufficiently small at −455 mV and the ESR value was minimized at 0.68; furthermore, change of the current was small and stable during the time proceeded.

According to the above result, it was determined that smaller particles produce better performance, and in particular, when ORP values of less than −400 mV are taken up to the standard, powder with a grain size of 150 μm or less is preferable. Moreover, it is more preferable to use powder with a grain size of 75 μm or less. It is considered that powder with grain sizes equal to or greater than 1 μm is available, because it is conjectured that powder with that size of grains maintains the surface characteristics proper to the powder materials.

FIG. 5 is a graph showing the change in performance when the amount of moisture in the waveform shaping device was varied. Specifically, a voltage of −6.03 kV was set at the input point of a waveform shaping device in which pumice stone powder with a grain size of 75 μm or less has been charged, and the output current and ORP values were monitored. Although the output voltage varied slightly according to conditions, the range between −5.85 kV and −5.96 kV can be used in a practically applicable range of the output voltage providing a large amount of output current.

The graph shows moisture content with volume % on the horizontal axis and ORP values on the vertical axis. From this graph, it can be determined that when the moisture percentage is 3%, the output current from the waveform shaping device increases and the ORP value is minimized. In particular, it is seen that in an extremely narrow range between moisture percentages of 2.7% and 3.1%, an extreme drop in ORP values is observed. Accordingly, it is preferable to maintain moisture percentage within a range of 2.5% to 3.5% including these minimized values.

In contrast to city water having the ORP value of +854 mV, FIG. 6 is a graph showing the observed changes in the ORP value of water produced by a negative ion producing device when the negative voltage applied to the waveform shaping device was varied. After energization for 25 minutes of the waveform shaping device according to the present embodiment assembled to a high negative voltage generator, the voltage in the waveform shaping device was plotted on the horizontal axis, and the ORP value thereof was plotted on the vertical axis; furthermore, the relationship between them was examined. From this graph, it was determined that the ORP value dropped suddenly between −3 kV and −4 kV, and thereafter, the value was maintained under −400 mV until −9 kV.

Furthermore, upon dilution of the samples by a predetermined ratio and investigation of the relative concentrations of dissolved hydrogen, it was seen that the concentration thereof was 0.8 ppb at −3 kV or less, 15.7 ppb at −4 kV, 16.0 ppb at −5 kV, 18.2 ppb at −6 kV, and approximately 20 ppb thereafter. Similarly, the ESR values were 3.37 at −4 kV, 1.93 at −5 kV, 1.35 at −6 kV, and gradually decreasing thereafter. From these figures, it was determined that the reducing action was sufficient between −5 kV and −9 kV, and that even between −3 kV and −5 kV, reducing action could be expected.

The optimum waveform shaping device obtained as a result of these tests is also optimum in terms of application to the human body. Human body by weight comprises 60% to 70% of water, and even in the cellular of the human body, 90% of the whole is occupied by water. Accordingly, in conditions where reducing action is strong to water in vitro, reducing action is also strong in vivo. The electric potential therapeutic appliance incorporating the optimum waveform shaping device obtained as a result of the tests described above was applied with respect to humans and the effectiveness of the appliance was observed.

FIG. 7 is a graph showing the effect of negative ions with respect to varying concentrations of 8-hydroxyl-deoxyguanosine (8-OHdG) in urine. Guanine in DNA changes to 8-OHdG when attacked by active oxygen produced in vivo, and is replaced to healthy guanine, released to blood and transferred to urine. Therefore, the concentration of 8-OHdG in urine acts as an index of the volume of in vivo active oxygen. Accordingly, the concentration of 8-OHdG in urine can be used to estimate the effect of negative ion action with respect to in vivo active oxygen.

An electric potential therapeutic appliance providing a waveform shaping device and a normal electric potential therapeutic appliance not including a waveform shaping device were prepared, and the graph compares results for a 12-person group exposed to negative ions using the electric potential therapeutic appliance providing a waveform shaping device and a 12-person control group using a normal electric potential therapeutic appliance. The negative ion irradiation group subjects were exposed to negative ions every 15 minutes for a period of 30 minutes, and 60 minutes and 120 minutes of the exposure indicated significant drops in the concentration of 8-OHdG by Wilcoxon testing with $P<0.01$.

Accordingly, it was determined that negative ions are directly produced in bodily liquid using an electric potential therapeutic appliance providing the waveform shaping device according to the present embodiment, resulting in powerful reducing action.

As a test for confirming curative effect, 14 healthy male subjects were separated into two groups, an electrode connected to an electric potential therapeutic appliance providing a waveform shaping device was applied to each subject with respect to one group, an electrode connected to an electric potential therapeutic appliance not providing a waveform shaping device was applied to each subject with respect to the other group, and negative ions were produced. Each test subject was not informed of which electric potential therapeutic appliance was used in his case.

Electric field exposure by electric potential therapeutic appliance was carried out by placing the left hand in contact with an electrode, and five times of 15-minute irradiations were performed over a 24-hour period. Blood samples were taken before and after exposure, and the activity of natural killer (NK) cells and metabolic factors of both inside and outside of red blood cells were examined.

Specifically, seven metabolic factors both intracellular and extracellular red blood cells were examined—namely, red blood cell ORP (RBC•ORP), blood ORP (BL•ORP), pH in red blood cell pH (RBC•pH), blood pH (BL•pH), lactic acid value within red blood cells/pyruvic acid value within red blood cells (Intra LA/Intro PA), venous blood carbon-dioxide concentration ($VPCO_2$), and venous blood oxygen concentration ($VPO_2$).

In order to simplify evaluation, each item was classified as excellent, good, or bad; points of 5, 3, and 1 were assigned respectively, the total points for each item were calculated, and comparison was made using this metabolic score. As a guide, scores of between 30 and 35 were evaluated as being good, scores of between 23 and 30 were evaluated as being normal, scores of between 18 and 23 were evaluated as being poor, and scores of 18 and lower were evaluated as being bad. NK cell activity is related to changes of the oxidation reduction potential both inside and outside of red blood cells. The supplied electrons pass from outside to inside of cells and reduce the ORP inside of the cells while the ORP outside rises slightly. It is thought that a drop in inner cellular ORP even occurs in NK cells, the mitochondria membrane potential in NK cells rises, and the NK cells become activated. Accordingly, the NK inner cellular ORP is replaced using the red blood cell inner cellular ORP, the values of (Red blood cell inner cellular ORP−blood ORP)/blood ORP or in other words (RBC ORP−BL ORP)/BL ORP were investigated, and a tendency for NK cell activity to increase when this value is less than prior to exposure was identified.

FIG. 8 through FIG. 10 show the results of comparison of the averages of results obtained for each group. FIG. 8 displays variations in the average measured values of pre-exposure and post-exposure NK cell activity for groups exposed using an electric potential therapeutic appliance with a waveform shaping device and for groups using an electric potential therapeutic appliance without a waveform shaping device, and it indicates the standard deviation value for each group. Furthermore, for the purpose of comparison, the results of therapy using electric potential therapeutic appliances known in the prior art and referred to as field-effect light ray therapy devices are also shown in the graph. In the case of each test, results from the examination of seven subjects were used. Differences in pre-exposure and post-exposure values were confirmed as being significant by Wilcoxon testing with $P<0.01$.

As can be seen in the graph, there is a significant increase in post-exposure NK cell activity when using an electric potential therapeutic appliance with the waveform shaping device. Meanwhile, when using an electric potential therapeutic appliance without the waveform shaping device, the NK cell activity exhibited a reduction in significance. From these results, it can be determined that an electric potential therapeutic appliance with the waveform shaping device is effective in increasing NK cell activity.

While a significant increase in NK cell activity can also be achieved after exposure by a field-effect light ray therapy devices known in the prior art, it was proved that the electric potential therapeutic appliance using the waveform shaping device according to the present invention produces a significantly larger increase in the post-exposure activity thereof, realizing a greater benefit of application.

With respect to pre-exposure and post-exposure values for electric potential therapeutic appliances with the waveform shaping device and electric potential therapeutic appliances without the waveform shaping device, FIG. 9 plots the metabolic score and FIG. 10 plots the values of the above equation (RBC ORP−BL ORP)/BL ORP.

In groups for which electric potential therapeutic appliances with the waveform shaping device were used, the post-exposure metabolic score increased and the post-exposure value of the above equation decreased. Both results are statistically significant with $P<0.01$. In contrast, in groups for which electric potential therapeutic appliances without the waveform shaping device were used, the averages of both of these values exhibited a change in the opposite direction. However, neither case was statistically significant.

In accordance with the above, the significant effect of waveform shaping devices even when used with respect to the human body was corroborated.

When compared with similar therapy devices known in the prior arts, an electric potential therapeutic appliance with the waveform shaping device according to the present embodiment realizes the effect of negative ions or reducing ions in vivo, producing considerable growth in the immune responsive cells therein, increasing attacks on virus-infected cells by the large amounts thereof, and contributing to the elimination or reduction of viruses. Accordingly, the electric potential therapeutic appliance according to the present embodiment is effective in the therapy of virus-infected patients with reduced immunity.

Therapy Example 1

Chronic Viral Hepatitis Infectious Disease

A subject patient had been infected for more than 15 years with hepatitis C virus. The patient usually exhibited abnormal values of GOT and GPT before therapy with the electric potential therapeutic appliance according to the present invention, and the amount of HCV-RNA copies in blood was 240 KIU/ml. The electric potential therapeutic appliance providing the waveform shaping device according to the present embodiment was used with respect to the subject patient, and 15-minute therapies were administered at least four times daily with an interval of approximately 1 hour there between by bringing both hands of the patient into contact with the probe electrode plates.

FIG. 11 is a graph showing the change of the number of HCV-RNA copies as a result of therapy. Specifically, therapy resulted in a drastic reduction in the number of HCV-RNA copies, and the number thereof dropped to 25 KIU/ml over a two-month period. Although omitted in the figure, the number of natural killer (NK) cell subsets was also increased by therapy using the electric potential therapeutic appliance according to the present invention from 60 per µl before therapy to 88 per µl after two weeks and to 92 per µl after two months. Accordingly, the remarkable benefit of therapy using the electric potential therapeutic appliance according to the present embodiment with respect to type C viral hepatitis was demonstrated.

Therapy Example 2

Human Immunodeficiency Virus (HIV) Infectious Disease

Reverse transcription inhibitors, HIV protease inhibitors, and the like are considered effective in the therapy of HIV infection. However, these chemical therapies are characterized by many cases of ineffectiveness, and in addition, severe side effects such as reduced numbers of white blood cells and blood platelets have been observed. Furthermore, even in the case of anti-HIV drugs, it is known that the emergence of drug tolerance strains causes to make the drug ineffective.

It was considered that HIV infection could also be treated using a similar mechanism to that of Therapy Example 1, and in order to confirm the validity of substitution thereof for chemical therapy methods, therapy was attempted using an electric potential therapeutic appliance providing the waveform shaping device according to the present embodiment. The subject HIV patient was a 29 year old female experiencing severe pains in the back, buttocks and lumber regions.

Figure 12:
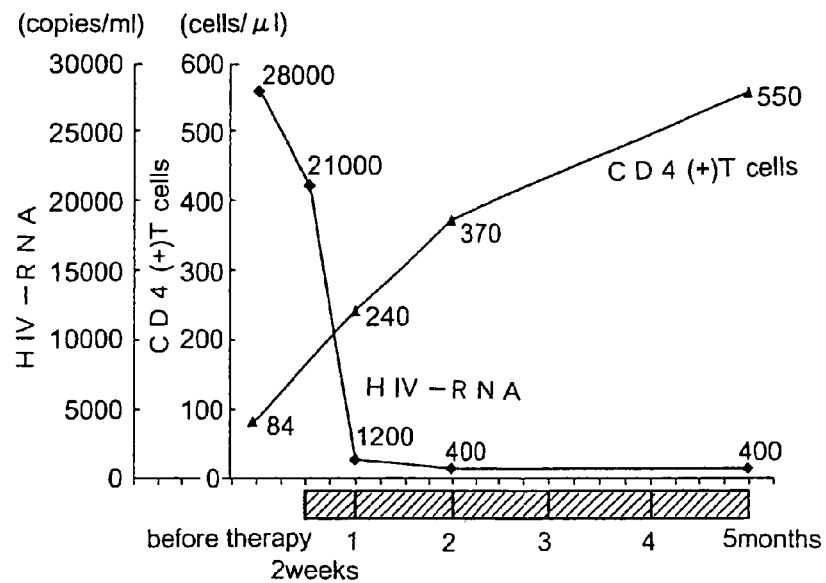
FIG. 12 is a graph showing the change over time of the number of HIV-RNA copies and CD4+ lymphocytes in the blood of a subject infected with HIV when therapy is administered using the electric potential therapeutic appliance of the present embodiment.

FIG. 12 is a graph tracing the change in the number of HIV-RNA copies and CD4(+) T lymphocytes over the course of therapy. Before the start of therapy using the electric potential therapeutic appliance according to the present invention, the amount of HIV-RNA copies was high at 28,000 copies per milliliter, and the number of CD4(+) T lymphocytes had dropped to 84 per µl. Over the initial two-week period, multidrug combination therapy including the use of HIV protease inhibitors was administered every day. Over the two-week period following this therapy, the number of HIV-RNA copies decreased to 21,000 per µl.

At this point, the electric potential therapeutic appliance according to the present invention was also introduced with the patient four or five times every day for individual periods of 15 minutes bringing both hands into fixed contact with the electrode plates. Over the one month period after the start of this therapy, the amount of HIV-RNA copies dropped radically to 1,200 per milliliter, and the number of CD4(+) T lymphocytes increased to 240 per µl. The severity of pains in back, buttocks and lumber regions was significantly reduced. After reducing the frequency of administration of multi-drug combination therapy from every day to five times a week, therapy was continued for another one month in combination with the electric potential therapeutic appliance, resulting in a reduction of HIV-RNA copies to below 400 per ml and of CD4(+) T lymphocytes to 370 per µl.

After an additional period of two months, the frequency of administration of multi-drug combination therapy was reduced to three times weekly; however, the amount of HIV-RNA remained at below 400 copies per ml, and the number of CD4(+) T lymphocytes returned to 550 per µl. Furthermore, the severe pains previously experienced in the back, buttocks and lumber regions had almost completely disappeared and the patient's lifestyle was no longer compromised in any way.

The phenomenon of CD4+ T lymphocytes dropping to a low level of 400 copies per µl through this type of multi-drug combination therapy is unusual, and even when the frequency of administration of chemical therapy was subsequently reduced, an antiviral effect was realized and the number of CD4+ T lymphocytes continued to increase, pointing to the considerable immuno-activation effect of the potential therapeutic appliance with the waveform shaping device.

The number of therapies per day, the duration of each individual therapy, and the interval therebetween are in no way dependent on the examples explained above, and suitable choices can be made in accordance with the patient's condition.

Figure 13:
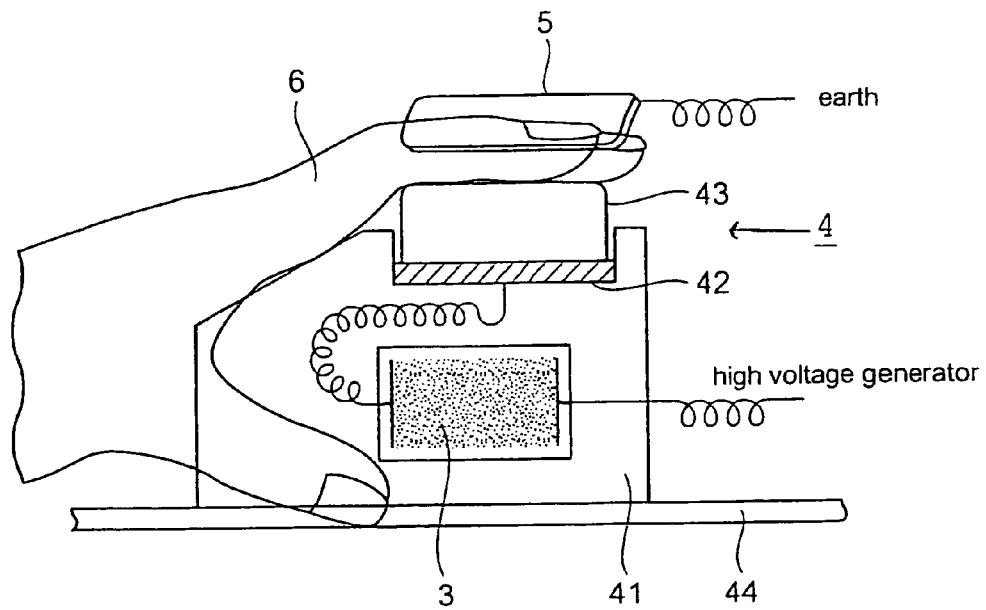
FIG. 13 is a conceptual illustration illustrating an example of a mode of use of the electric potential therapeutic appliance of the present embodiment.

FIG. 13 shows an example of the potential therapeutic appliance according to the present invention being used on a human subject. When using the device shown in FIG. 13, one or more fingers are inserted between the probe electrode plates thereof, so that reducing ions can be produced in the blood, realizing one of the simpler therapy methods.

A therapy box 41 containing the waveform shaping device 3 and the negative terminal plate 4 is provided. The negative probe electrode plate 4 is constituted by conductive rubber 43 disposed on top of an aluminum plate 42, and one or more fingers 6 of the subject are placed on the conductive rubber 43 and secured in place by the ground probe electrode plate 5 placed on top thereof. The therapy box 41 is disposed on top of an insulating rubber plate 44.

High negative voltage signal provided from the output terminals of a high voltage generator is directed to the probe electrode plate 4 after shaping thereof by the waveform shaping device 3, forming an electrical field with a specified waveform between the ground probe electrode plate 5 and the conductive rubber 43, and producing reducing ions in the finger(s) 6.

The ground probe electrode plate 5 is constituted by a terminal plate formed of conductive rubber and coated with insulating rubber; accordingly, adhesive gel may be used to improve the contact thereof with the finger(s) 6.

With this type of configuration, therapy can be simply administered to finger(s) by simple placing thereof on a table.

Figure 14:
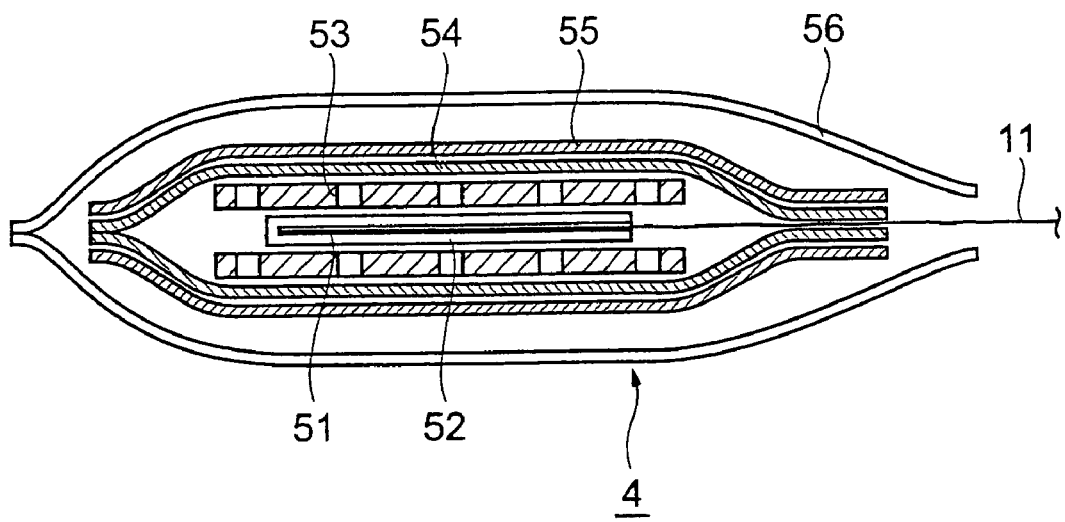
FIG. 14 is a conceptual illustration illustrating an example of the construction of a different negative probe electrode plate used in the electric potential therapeutic appliance of the present embodiment.

FIG. 14 is a cross-section view illustrating the construction of a different example of negative probe electrode plate.

A brass electrode plate 51 is wrapped in a PVC bag 52; insulating rubber plate 53 formed with appropriately spaced through-holes encloses the PVC bag 52 on two opposing sides; and insulating rubber plates 53 are inserted into a bag comprising washleather 54 and quilting 55, the outermost layer thereof being wrapped in a cotton bag 56.

Since the electrode plate 51 is constituted by brass of a thickness of between 0.1 mm and 0.3 mm, the shape thereof can be easily modified to match the shape of the part of the body to which the probe electrode plates are applied, enabling suitable contact to be made with the body surface.

In addition, the PVC bag, the insulating rubber plates, the soft leather, the quilting, and the cotton bag are disposed between the terminals and the body surface, improving the cushioning effect and promoting more comfortable contact with the skin.

When the insulating rubber plates are provided without through-holes, production of reducing ions in the human body becomes difficult to achieve. In contrast, by providing appropriate through-holes in the insulating rubber plates 53 and by forming air layer portions therein, the degree of electrical resistance or resistance of ion flight can be adjusted as appropriate, and this thought to be effective in achieving a suitable volume of reducing ions applied to, or produced in, the human body.

When applying the potential therapeutic appliance according to the present invention with respect to the human body, the negative probe electrode plate and the ground probe electrode plate are fixed in contact with a portion of the subject's body such as the hand, the potential therapeutic appliance is turned on, the therapy time is set, and therapy is started. When the set time has expired, the production of negative ions ends automatically, the therapy is then ended by removing the probe electrode plates. This represents one of the simplest such therapy methods.

In addition, the probe electrode plates making contact with the body have a construction comprising insulating rubber and conductive rubber layered on a metal terminal plate, and the current can be controlled to as little as between 0.1 and 10 µA, ensuring the safety of the subject.

It is important that both probe electrode plates are disposed in positions where the probe electrode plates make contact with the body surface, for example, the patient's abdomen, back, or shoulders.

It is particularly recommended that the palm be enclosed between the ground side probe electrode plate and the negative probe electrode plate. The palm is relatively thin and contains a large flow of blood; accordingly, this configuration is characterized by a small distance between the probe electrode plates, a strong electric field, and a significant effect achieved through powerful action on a large volume of blood. Furthermore, as the hand is normally exposed, the probe electrode plates can be easily applied thereto, reducing the burden placed on patients and technicians.

Using a potential therapeutic appliance providing several pairs of output terminals featuring similar functionality, several pairs of probe electrode plates can be simultaneously applied. It is understood that the use of two pairs of probe electrode plates is generally more effective than the use of a single pair thereof.

What is claimed is:

1. A therapy method for chronic virus infectious disease comprising:
    a step of providing an electric potential therapeutic appliance, the electric potential therapeutic appliance comprising,
    a high voltage power source having a negative terminal for configured to output a high voltage negative electric power of between −3 kV and −9 kV,
    a waveform shaping device provided with an insulating case having a first pair of electrode plates, comprising a first negative electrode plate and a first positive electrode plate, disposed in opposition within the insulating case and filled with porous silica powder with a grain size of between 1 µm and 200 µm and moisture by volume between 2.5% and 3.5% between the electrode plates, wherein a negative terminal of the high voltage power source is connected to an input terminal of the waveform shaping device,
    wherein the waveform shaping device receives the high voltage negative electric power output by the high voltage power source, deforms the high voltage negative electric power via capacitive discharge and outputs the deformed high voltage negative power signal via an output terminal of the waveform shaping device as a waveform shaping device output voltage signal having a predetermined waveform;
    a step of providing a second pair of electrode plates comprising a second negative electrode plate connected to the output terminal of the waveform shaping device and a second positive electrode plate connected to the ground terminal of the high voltage power source;
    a step of placing a part of a patient's body between the second pair of electrode plates;
    a step of increasing an amount of immunocompetent cells in the patient's body by exposing the part of the patient's body to the waveform shaping device output voltage signal for a predetermined duration via the second pair of electrode plates.

2. The therapy method of claim 1, wherein the step of placing a part of the patient's body between the second pair of electrode plates comprises placing a first palm of the patient between the second pair of electrode plates, and further comprising:
    a step of providing a third pair of electrode plates comprising a third negative electrode plate connected to the output terminal of the waveform shaping device and a third positive electrode plate connected to the ground terminal of the high voltage power source; and
    a step of placing a second palm of the patient between the third pair of electrode plates;
    wherein the step of exposing the part of the patient's body to the waveform shaping device output voltage signal comprises exposing the first and second palms of the patient to the waveform shaping device output voltage signal for a predetermined duration via the second and third pair of electrode plates, respectively.

3. A therapy method for chronic virus infectious disease comprising:
    a step of providing an electric potential therapeutic appliance, the electric potential therapeutic appliance comprising,
    a high voltage power source having a negative terminal configured to output a high voltage negative electric power of between −3 kV and −9 kV,
    a waveform shaping device provided with an insulating case having a first pair of electrode plates, comprising a first positive electrode plate and a first negative electrode plate, disposed in opposition within the insulating case and filled with porous silica powder with a grain size of between 1 µm and 200 µm and moisture by volume between 2.5% and 3.5% between the electrode plates, wherein a negative terminal of the high voltage power source is connected to an input terminal of the waveform shaping device,
    wherein the waveform shaping device receives the high voltage negative electric power output by the high voltage power source, deforms the high voltage negative electric power via capacitive discharge and outputs the deformed high voltage negative power signal via an output terminal of the waveform shaping device as a waveform shaping device output voltage signal having a predetermined waveform;
    a step of providing a second pair of electrode plates comprising a second negative electrode plate connected to the output terminal of the waveform shaping device and a second positive electrode plate connected to the ground terminal of the high voltage power source;
    a step of placing a part of a patient's body between the second pair of electrode plates;
    a step of treating chronic virus infectious disease by exposing the part of the patient's body to the waveform shaping device output voltage signal for a predetermined duration via the second pair of electrode plates.

4. The therapy method of claim 3, wherein exposing the part of the patient's body to the waveform shaping device output voltage signal for a predetermined duration via the second pair of electrode plates increases the amount of immunocompetent cells in the patient's body.

5. A therapy method for chronic virus infectious disease comprising:
    providing an electric potential therapeutic appliance, the electric potential therapeutic appliance comprising,
    a high voltage power source having a negative terminal configured to output a high voltage negative electric power of between −3 kV and −9 kV,
    a waveform shaping device provided with an insulating case having a first pair of electrode plates, comprising a first negative electrode plate and a first positive electrode plate, disposed in opposition within the insulating case and filled with an inorganic substance in powder form and a certain amount of moisture predetermined in accordance with the capacity of the insulating case, wherein a negative terminal of the high voltage power source is connected to an input terminal of the waveform shaping device, wherein the waveform shaping device receives the high voltage negative electric power output by the high voltage power source, deforms the high voltage negative electric power via capacitive discharge and outputs the deformed high voltage negative power signal via an output terminal of the waveform shaping device as a waveform shaping device output voltage signal having a predetermined waveform;

providing a second pair of electrode plates comprising a second negative electrode plate connected to the output terminal of the waveform shaping device and a second positive electrode plate connected to the ground terminal of the high voltage power source;

placing a part of a patient's body between the second pair of electrode plates;

increasing an amount of immunocompetent cells in the patient's body by exposing the part of the patient's body to the waveform shaping device output voltage signal for a predetermined duration via the second pair of electrode plates.

* * * * *